United States Patent [19]

Thomas et al.

[11] Patent Number: 4,874,251
[45] Date of Patent: Oct. 17, 1989

[54] THERMAL WAVE IMAGING APPARATUS

[75] Inventors: Robert L. Thomas, Huntington Wood; Pao-Kuang Kuo, Troy; Lawrence D. Favro, Huntington Wood, all of Mich.

[73] Assignee: Wayne State University, Detroit, Mich.

[21] Appl. No.: 808,350

[22] Filed: Feb. 10, 1986

Related U.S. Application Data

[63] Continuation of Ser. No. 596,515, Apr. 4, 1984, Pat. No. 4,589,783.

[51] Int. Cl.[4] .................... G01N 21/00; G01N 25/00
[52] U.S. Cl. ..................................... 374/45; 250/334; 356/128; 374/124; 374/128
[58] Field of Search .................. 374/45, 121, 128, 112; 250/205; 356/128; 358/113; 364/557

[56] References Cited

U.S. PATENT DOCUMENTS

| | | | |
|---|---|---|---|
| 3,018,331 | 1/1962 | McConnell | 250/205 X |
| 3,715,922 | 2/1973 | Menge | 374/128 X |
| 3,859,539 | 1/1975 | Allington | 250/205 X |
| 4,243,327 | 1/1981 | Frosch et al. | 374/5 X |
| 4,308,585 | 12/1981 | Jordan | 364/520 |
| 4,468,136 | 8/1984 | Murphy et al. | 45/ |
| 4,579,463 | 4/1986 | Rosencwaig et al. | 374/5 X |
| 4,589,783 | 5/1986 | Thomas et al. | 374/6 X |

FOREIGN PATENT DOCUMENTS

873747 11/1979 U.S.S.R. .............. 374/128

Primary Examiner—Daniel M. Yasich
Attorney, Agent, or Firm—Arnold S. Weintraub; Gerald R. Black

[57] ABSTRACT

A thermal wave imaging apparatus generates a real time image of the surface and subsurface of an opaque solid object. A.C. electrical signals indicative of the configuration of the surface and subsurface of the object which are generated during a thermal wave scan of the object by a first heating beam which generates a localized temperature gradient on the object and a deflectable second probe beam heating beam, which deflection is detected by a detection device mounted adjacent to the object, are stored in an image memory under the control of a central processor. A refresh counter generates sequential, incremental signals used to control the X and Y axis deflection of a display monitor. Such signals also address the image memory and generate output data controlling the intensity of the display point at each generated X and Y axis deflection point. A modulation and intensity regulation circuit generates an optical beam having a constant amplitude in spite of any fluctuations in the output of the heating laser.

4 Claims, 4 Drawing Sheets

THERMAL WAVE IMAGING APPARATUS

REFERENCE TO RELATED APPLICATION

This application is a 37 C.F.R. 1.60 continuation of application No. 596,515 filed on Apr. 4, 1984, now U.S. Pat. No. 4,589,783.

BACKGROUND OF THE INVENTION

1. Field of the Invention:

This invention relation, in general, to methods and devices for non-destructive testing of opaque articles to detect surface and sub-surface cracks, flaws, voids, etc.

2. Description of the Prior Art:

Various methods have been proposed to detect surface and subsurface cracks, flaws, voids, etc., in opaque solids. One common method utilizes photo-acoustic techniques in which periodic, localized heating of a sample within a gas-filled cell is caused by focused intensity modulated light, electro-magnetic radiation or a particle beam. The heat generates sound within the gas medium which is detected by a transducer, such as a microphone mounted within the gas cell. The transducer or microphone generates electrical signals which are analyzed to locate surface and subsurface defects.

In actual use, an argon-ion laser whose output is modulated is focused onto the surface of interest through an optical window spaced from the surface of the sample by a small volume of air of gas. The transducer mounted within the cell detects the amplitude and phase of pressure variations with the cell caused by the temperature profile at the surface of the sample. However, while the imaging technique is effective at detecting certain crack orientations, it cannot detect strictly vertical, closed cracks. While in practice many cracks are not quite vertical or not quite closed or both, any cracks which are strictly vertical and closed would be missed when employing this technique.

Mirage effect thermal wave imaging has proven effective at detecting strictly vertical closed cracks within opaque solids. This technique utilizes a laser to probe the air just above the surface of an opaque solid which is heated by a second modulated laser. An A.C. electrical signal is produced by using a phototransistor to monitor the deflection of the probe beam in a plane parallel or perpendicular to the sample surface. Indexing of the sample underneath the heating laser beam or indexing the heating laser beam over the surface of the sample results in a series of data signals which are useful in detecting subsurface and surface cracks, flaws, voids and other defects.

Other imaging techniques currently being used or investigated include gas cell, photothermal displacement, infrared detection and piezoelectric detection.

The signals by themselves cannot yield any useful information as to the existence of surface or subsurface cracks without additional analysis. Heretofore, on-line, real time analysis techniques have been minimal for data generated by the various thermal wave imaging techniques. This lack of useful data analysis techniques has hampered the use of thermal wave imaging techniques for detecting surface and subsurface cracks in opaque solid objects.

Thus, it would be desirable to provide an analysis technique which overcomes the deficiencies in analyzing and displaying information generated during a thermal wave scan of opaque solids. It would also be desirable to provide an analysis technique for use with a thermal wave scan of opaque solids which generates a visual image of the surface and immediate subsurface of the solid illustrating any cracks, flaws, which may exist within the solid. Finally, it would be desirable to provide an analysis technique for use with thermal wave imaging of opaque solids which generates a visual image of the existence of any cracks or flaws within the sample during real time when the sample is being probed by the thermal wave scan.

SUMMARY OF THE INVENTION

There is disclosed a unique thermal wave imaging apparatus which includes unique data acquisition features for generating an on-line, real-time image which is useful in detecting the presence of any surface or subsurface cracks, flaws or voids in an opaque solid object.

The thermal wave imaging apparatus of the present invention can be used with any imaging process including gas cell, photothermal displacement, mirage effect, infrared detection, piezoelectric detection and photoacoustic detection. By way of example only, the present invention will be described in use with a mirage effect imaging apparatus.

As is conventional, in the mirage effect technique, a heating laser generates an output which is intensity modulated to provide a periodic optical signal used to periodically heat a point on the surface of an object. The optical beam from a probe lase passes parallel to the surface of the object through the heated zone. This probe beam is deflected from a normal path due to density variations in the air above the surface of the sample caused by uneven heating due to the presence of surface or subsurface cracks, flaws, voids, etc., in the object. The amount of deflection of the probe beam is detected to provide an indication of the existence of any surface or subsurface defects in the object.

According to the present invention, the deflection data are converted to digital signals and stored in an image memory under the control of a central processor. The stored defection data is used to control the intensity of points or pixels on a display monitor.

Separate means are provided for generating sequential, incremental signals used to control the X and Y axis defection of the monitor. Such signals are also used to address the image memory and to output therefrom the stored data at each address location corresponding to each generated X and Y deflection datum to control the intensity of the displayed point or pixel on the monitor. In this manner, as the object is probed point by point across its surface, a real time, on-line image is generated on the monitor which provides a visible indication of the presence of any surface or subsurface cracks, flaws, voids, etc. in the object.

The thermal wave imaging apparatus of the present invention also includes a unique beam modulation and intensity regulation circuit which controls an acousto-optic modulator such that the intensity or amplitude of the heating optical beam directed onto the surface of the object remains constant despite any fluctuations or variations in the output of the heating laser itself.

The thermal wave imaging apparatus of the present invention overcomes many of the deficiencies of previously devised techniques for analyzing data generated by various thermal wave imaging techniques. The data acquisition apparatus of the present invention uniquely enables a real time, on-line image to be generated to provide a visible indication of the presence of any surface or subsurface cracks, flaws, voids, etc. in the object.

BRIEF DESCRIPTION OF THE DRAWING

The various featues, advantages and other uses of the present invention will become more apparent by referring to the following detailed description and drawing in which.

DESCRIPTION OF THE PREFERRED EMBODIMENTS

Throughout the following description and drawing, an identical reference number is utilized to refer to the same component shown in multiple figures of the drawing.

The thermal wave imaging apparatus of the present invention is configured to control the acquisition of data during a thermal wave scan of an opaque solid object and to display an image of surface and subsurface images of the object showing any cracks, flaws, void or other defects in the surface and subsurface of the object. The apparatus of the present invention may be used with any imaging technique including, but not limited to, gas cell monitoring, photothermal displacement, mirage effect detection, and infrared detection, photoacoustic and piezoelectric monitoring. In each of these imaging techniques, A.C. electrical signals are generated by a detector, such as a microphone or phototransistor, which can be analyzed to provide information about the structure of the object.

By way of example only, the apparatus of the present invention will be described in conjunction with apparatus for using the mirage effect thermal wave imaging technique. It will be understood, however, that the present invention may be employed with any thermal wave imaging apparatus.

Before describing in detail a preferred construction of the thermal wave imaging apparatus of the present invention, a brief description of the theory behind the mirage effect technique for thermal wave imaging will be described to provide a basic understanding of principles employed in the thermal wave imaging techniques.

Figure 1:
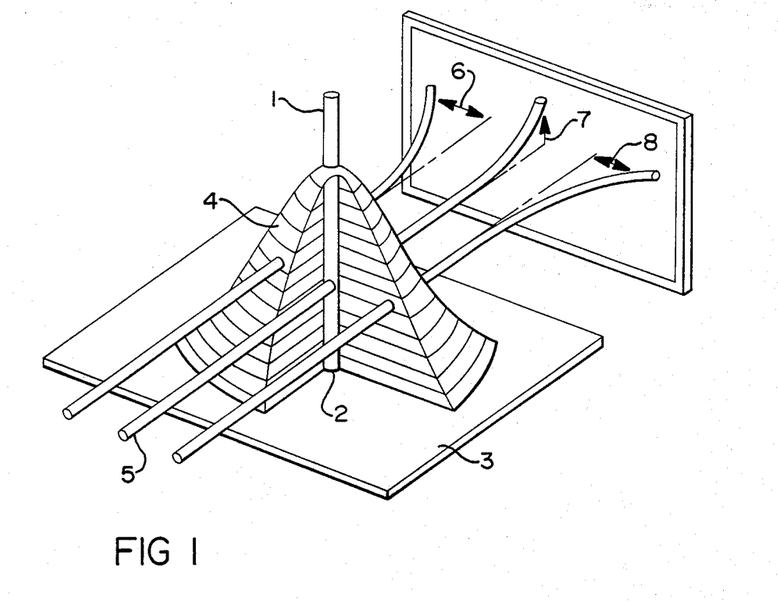
FIG. 1 is a pictorial representation of the temperature profile generated by a mirage effect thermal wave imaging technique.

According to the mirage effect method of thermal wave imaging, as shown in FIG. 1, an optical or laser heating beam 1 is utilized to provide periodic, localized heating of a point 2 on a opaque solid object 3. Such teaching of the object 3 creates a temperature profile 4 above the surface of the object 3 in which the density of the air just above and around the laser focal spot varies with temperature variations on the surface which in turn are influenced by variations in the adjacent subsurface of the object. Thus, the presence of cracks, flaws, or voids on the surface or immediately below the surface of the object 3 will cause density variations in the air above the surface of the object 3.

A probe beam 5 passing through this temperature profile parallel to the surface of the object 3 will be deflected by such density changes in the air immediately above the surface of the object 3. Detection of the deflected beams 6, 7 and 8 of the probe beam 5 can be utilized to provide an indication of the presence of a surface or subsurface crack, etc.

Figure 2:
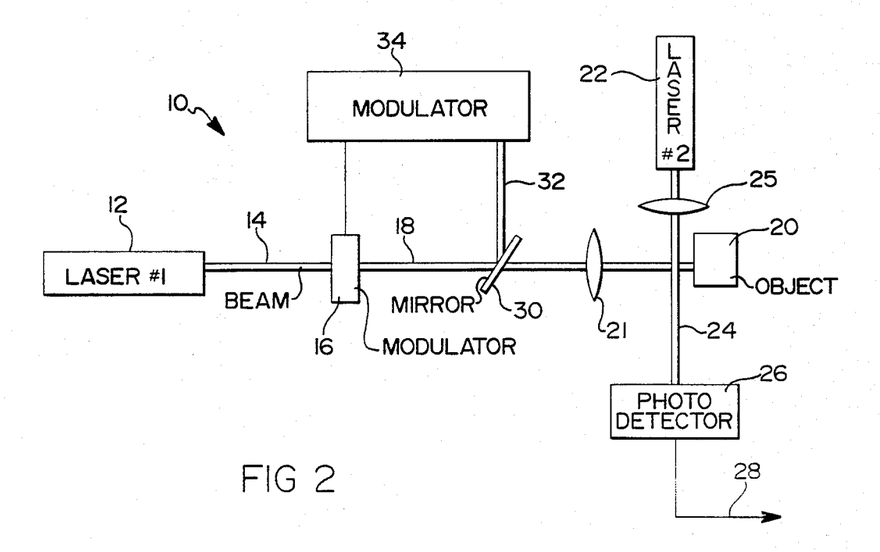
FIG. 2 is a block diagram showing a mirage effect thermal wave imaging apparatus; constructed in accordance with the teachings of the present invention

Referring now to FIG. 2, there is illustrated a thermal wave imaging apparatus 10 which is constructed to make use of the mirage effect to detect surface and subsurface cracks, etc., in an opaque solid object. The apparatus 10 includes a first heat source 12, such as a laser. Any type of laser 12 such as an argon-ion laser, may be employed in the apparatus 10. Furthermore, the laser 12 may be provided with any power output and in any wave length. Preferably, however, visible wave length are employed for ease in aligning and adjusting the apparatus 10.

As the laser 12 provides a continuous output beam 14, the beam 14 must be periodically interrrupted or modulated to provide the desired periodic, localized heating of the object. Thus, the output beam 14 from the laser 12 is passed through an acousto-optical chopper or modulator 16, whose output is a modulated optical beam 18. The beam 18 is directed onto an object 20 through a lens 21 to cause the desired periodic localized heating of a point on the surface of the opaque, solid object 20.

A second probe laser 22 is oriented such that its output beam 24 focused by a lens 25 passes through the heated area or temperature profile generated by the first laser 12 and substantially parallel to the surface of the object 20. As noted above, deflections of the output beam 24 caused by density variations in the air immediately above the surface of the object 20 can be detected by means of a photodetector 26, such as photodiode array. As is conventional, the photodiode array 26 includes two pairs of perpendicularly oriented photodiodes. The diodes in each pair are electrically connected such that an output signal will be generated which will indicate by means of its magnitude the point on the photodetector 26 on which the probe beam 24 impinges.

According to one feature of the subject invention, the thermal wave imaging apparatus 10 is provided with a feedback circuit to provide a constant output amplitude for the modulated laser beam 18 despite any fluctuations or variations which may occur in the output beam 14 of the heating laser 12. In effecting this feedback, a portion of the optical beam 18 from the modulator 16 is split by means of a conventional beam splitter 30, such as a partially reflective mirror, which deflects a portion 32 of the optical beam 18 to a beam modulator and intensity regulation circuit 34.

In general, the beam modulator and intensity regulation circuit 34 controls the modulator 16 in such a way that the amplitude of the output beam 18 remains constant inspite of any fluctuations or variations in the intensity of the output optical beam 14 generated by the laser 12.

Figure 3:
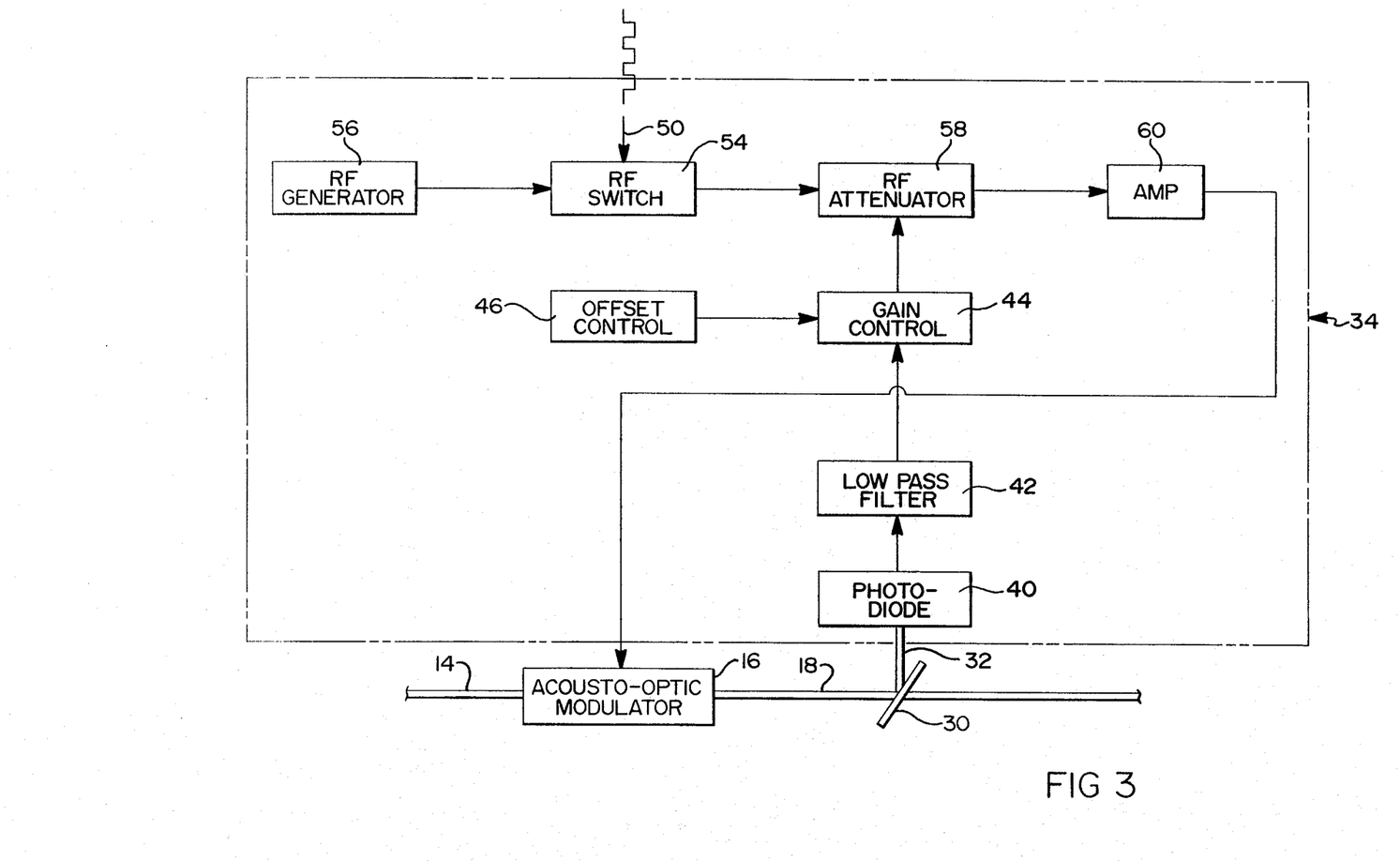
FIG. 3 is a block diagram of the laser beam modulator and intensity regulation circuit shown in general in FIG. 2.

As shown in greater detail in FIG. 3, the split portion 32 of the optical beam 18 strikes a photodiode 40 which generates an electrical output signal proportional to the intensity or amplitude of the beam 32. The output from the photodiode 40 passes through a low-pass filter circuit 42 to a gain control circuit 44. Another input to the gain control circuit 44 is a signal from an offset control circuit 46 to provide reference levels for the feedback signal.

At the same time, a square wave signal 50 at the desired modulation frequency is fed to a conventional RF switch 54 which modulates the output signal from a RF signal generator 56. The amount of RF signal which is passes to the modulator 16 is determined by means of an RF attenuator circuit 58 which receives the modulated RF signal from the RF switch 54 and the output of the gain control 44, with the magnitude of the output of the gain control 44 being proportional to the difference between the output signal from the low-ass filter 42 and the d.c. level of the signal from the offset control 46. The output of the attenuator 58 is amplified through and fed an amplifier to the acousto-optic modulator 16.

The acousto-optic modulator 16 is constructed in a conventional manner to diffract a portion of the input optical laser beam 14 into the output beam 18 only when an RF signal is present. In the absence of an RF signal as determined by the RF switch 54 described above, the output optical beam 18 is interrupted. In the presence of an RF signal, the intensity of the output beam 18 is controlled to a fixed level set by the d.c. offset control 46. In this manner, the intensity of the output optical beam 18 from the acousto-optic modulator 16 remains constant despite any fluctuations or variations in the output optical beam 14 from the laser 12.

Figure 4:
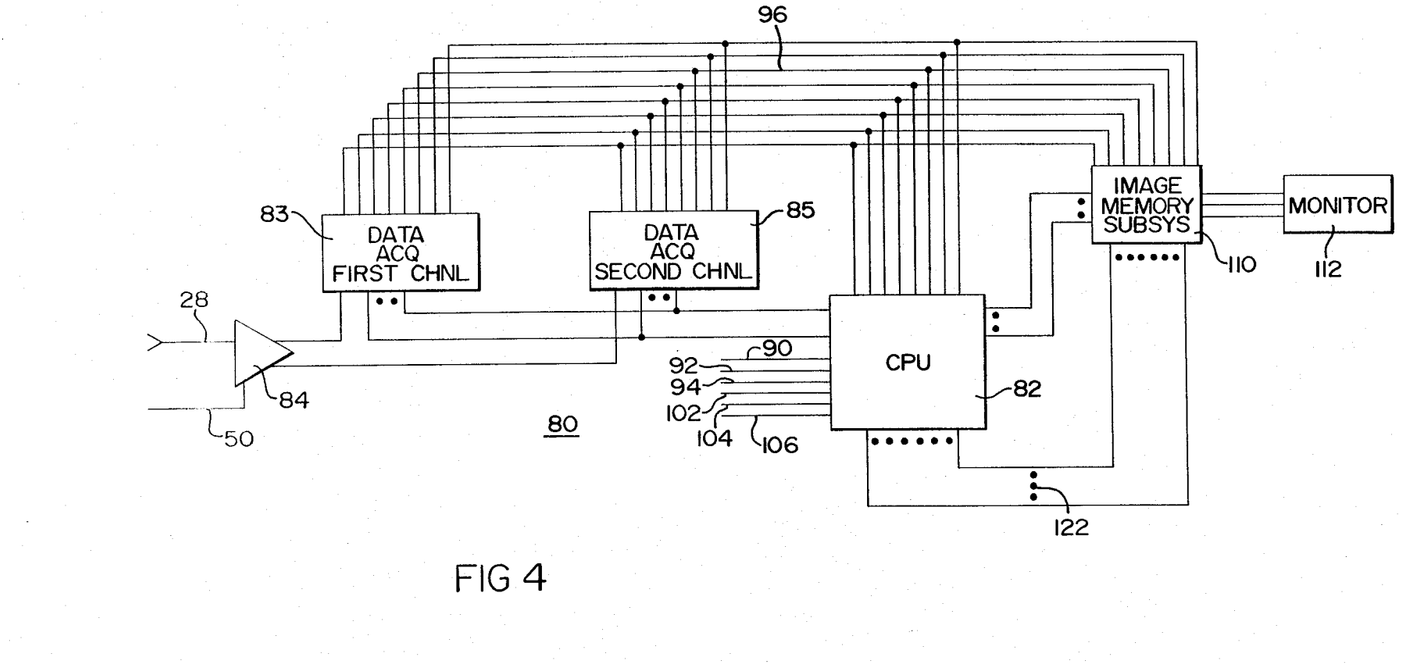
FIG. 4 is a block diagram showing the data acquisition and imaging system of the present invention.

Referring now to FIG. 4, there is illustrated a block daigram of a data acquisition and control system 80 which controls the acquisition of data from the photodetector 26 and the generation of a visible image which displays the presence of any surface or subsurface cracks, etc., on the object 20. The data acquisition system 80 is controlled by a central processor unit 82 which can be any conventional microprocessor, such as a microprocessor sold by Motorola Corporation, Model No. 6800. The central processor 82 controls the transfer of data between the various subsystems of the data acquisition system 80 by generating appropriate timed, control signals. In controlling such data transfer, the central processor 82 executes a stored control program shown in Appendix A.

As illustrated in FIG. 4, the output 28 from the photodetector 26 together with the reference signal 50 is input to a lock-in amplifier 84 which generates two outputs, one indicating the magnitude of the output from the photodetector 26 and the other the phase of the output signal from the photodetector 26 relative to that of the reference signal 50. Alternately, the two outputs can indicate the in-phase and quadrature components of the output from the photodiode 26. The outputs from the amplifier 84 are input to two separate data acquisition channels 83 and 85. labeled channel one and channel two, respective, corresponding to the phase and magnitude or the in-phase and quadrature outputs from the photodetector 26.

Figure 5:
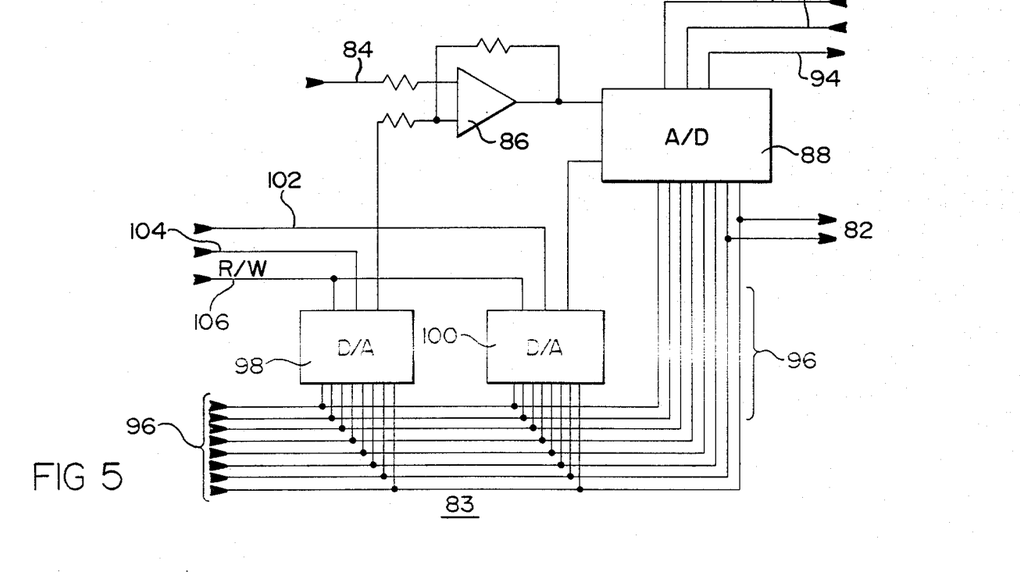
FIG. 5 is a detailed schematic and block diagram of one data acquisition channel.

Only one of the data acquisition channels 83 and 85, such as the first channel 83 corresponding to the magnitude signal from the photodetector 26, will be described in greater detail hereafter since both data acquisition channels 83 and 85 are identically constructed. As shown in FIG. 5, the output from the amplifier 84 is, in turn input to an amplifier 86 whose output is input to an A/D converter 88.

The A/D converter 88 is assigned to three address locations of the central processor 82, one for starting analog conversion, one for reading the busy state of the A/D converter 88 and a third for reading the converted data. In operation, the central processor 82 initiates a data conversion by sending a signal on control line 92 to the A/D converter 88, waits for a busy state completion signal on control line 94 from the A/D converter 88 and then generates a read data signal on control line 90. The output from the A/D converter 88 is input on data bus lines 96 to the central processor 82.

The output data signals from the central processor 82 on lines 96 are input to two D/A converters 98 and 100. Each of the D/A converters 98 and 100 is assigned a single address and behaves as a random access memory for the central processor 82. A number written in the D/A converter 98 is converted into an analog voltage which is summed by the amplifier 86 with the analog input signal from the lock-in amplifier 84. This provides a programmable offset. Control line 104 is the chip select line and line 106 is the read/write control line for this operation. In a similar fashion, the D/A converter 100 provides a programmable voltage which is input to the A/D converter 88 as a reference voltage for conversion, thereby providing a programmable gain control. Control lines 102 and 106 are the control lines for this operation.

Referring again to FIG. 4, the output data from the first data acquisition channel 83 is transferred under the control of signals generated by the central processor 82 to an image memory subsystem 110. The image memory subsystem 110 serves as an image memory for a digitized microscopic picture of the object 20. The output of the memory contained with the image memory subsystem 110 is continuously displayed on a monitor 112 which, in a preferred embodiment, is a high resolution, flat screen display with a linear intensity response so as to generate a high quality picture suitable for photography. Furthermore, the data content of the image memory subsystem 110 is displayed in gray scale on the monitor 112 with 256 different intensity levels for each pixel and a total of 65,536 pixels.

In general, the basic cycle of the central processor 82 is divided into two halves, with the central processor 82 addressing memory only during the first half of each cycle. Then, during the second half of each cycle, the address lines of the memory are multiplexed to the output of a 16-bit refresh counter which is constantly incremented by the CPU clock.

Figure 6:
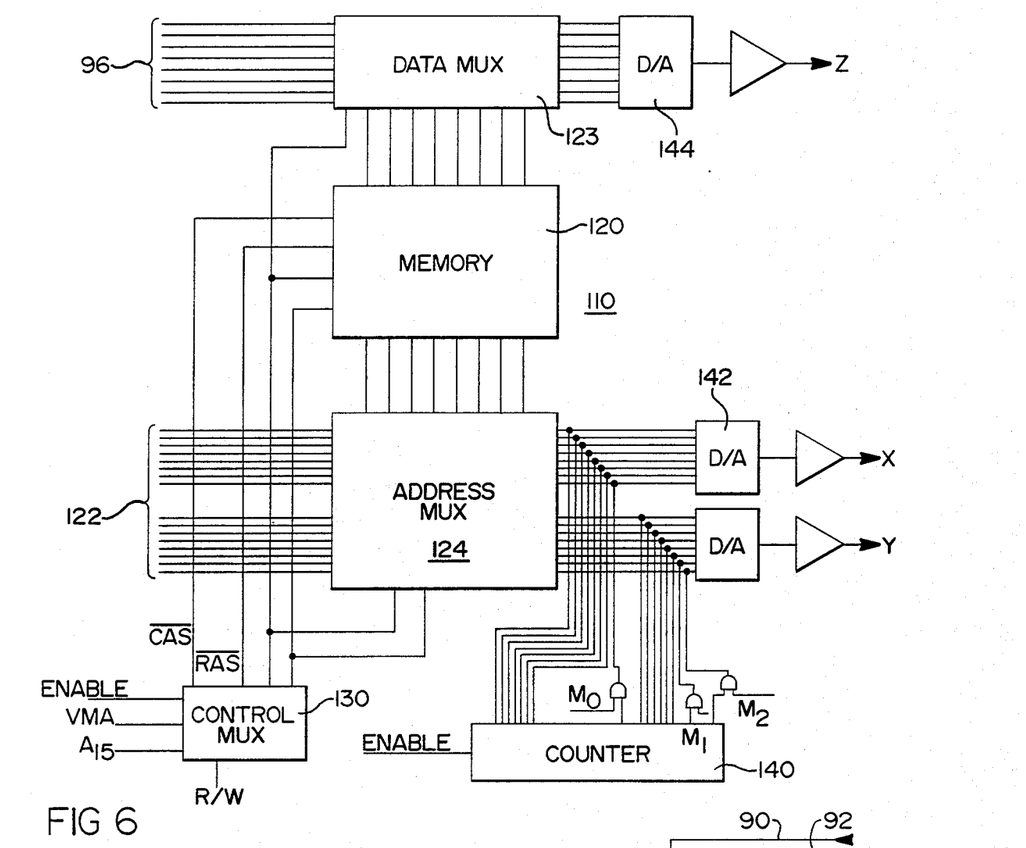
FIG. 6 is a schematic and block diagram of the image memory subsystem shown in general in FIG. 4.

Referring now to FIG. 6, there is shown a detailed block diagram of the image memory subsystem 110. The image memory subsystem 110 includes a random access memory 120 which, in a preferred embodiment, includes 64K of 8 bit memory locations. During each half cycle, the central processor 82 will generate sequential addresses on address bus 122 which are input to an address multiplexer 124. The address multiplexer 124 controls the selection of addresses to be used to address the memory 120. During the memory read or write half cycle of the central processor 82, the address multiplexer 124 will select addressed from address bus 122 so as to direct the data on data bus 96 to the appropriate locations within the memory 120.

As shown in FIG. 6, the data bus 96 is also input to a data line multiplexer 128 which controls the flow of data either between the central processor 82 and a memory 120 or between the memory 120 and the D/A converter 144.

In this manner, data corresponding to the magnitude or phase of the deflection of the probe beam for each sequentially sampled spot on a surface of the object 20 is stored in sequential memory locations within the memory 120. The magnitude or phase of the deflection of the probe beam corresponds to the intensity of the displayed point image on the monitor 112. In a preferred embodiment, the two data acquisition channels 83 and 85 operate in parallel so that both magnitude and phase images appear on the monitor 112 simultaneously. Alternately, only one of the channels 83 and 85 may be activated to display only a single image.

The image memory subsystem 110 also includes a control multiplexer 130 which controls the read-write mode of the memory 120 as well as the selection of addresses by the address multiplexer 124 and the data multiplexer 128.

A 16-bit refresh counter 140 generates a new 16-bit address upon each ENABLE signal from the central processor 82. The address multiplexer 124 will select the output from the 16-bit counter 140 during each nonread or write half cycle of the central processor 82. The output of the counter 140 is input to two D/A converters 142 which convert two 8-bit signals from the counter 140 to two signals used to control the X and Y axis deflection of the monitor 112. This controls the position of the next point to be displayed on the monitor 112. At the same time, the address generated by the counter 140 is input through the address multiplexer 124 to the memory 120. Data stored at the specified address location is output through the data line multiplexer 128 to D/A converter 144. The output signal from the D/A converter 144 is amplified and fed to the monitor 112 to control the intensity of the point being displayed on the monitor 112.

Also shown in FIG. 6 are mode control signals $M_0$, $M_1$ and $M_2$ are input to gates 146, 148 and 150. The mode control signals $M_0$, $M_1$ and $M_2$ are generated by the central processor 82 and are used to control the size of the display image on the monitor 112. For small sample sizes, only one-eight, one-quarter or one-half of the display screen need be used. Thus, depending upon the binary code input on lines $M_0$, $M_1$ and $M_2$ to the selected mode control gates 146, 148 and 150, only one-eighth, one-quarter, one-half or a full screen will be displayed. When a partial screen on the monitor 112 is displayed, the monitor 112 will be refreshed at a faster rate which reduces any flickering of the image.

In summary, there has been disclosed a unique thermal wave imaging apparatus which generates an on-line, real time image of surface and subsurface cracks, flaws, etc., on an opaque solid which is probed by means of a thermal wave imaging technique. A laser beam modulation and regulation control circuit has also been disclosed which generates a modulated optical beam of a constant amplitude or intensity inspite of an fluctuations or variations in the output beam of a laser.

APPENDIX A
BINARY LISTING OF CONTROL PROGRAM (Binary hex dump listing omitted due to density; addresses C000 through C4C8 in 8-byte rows.)

APPENDIX A-continued
BINARY LISTING OF CONTROL PROGRAM

| | | | | | | | | | | | | | | | | | |
|---|---|---|---|---|---|---|---|---|---|---|---|---|---|---|---|---|---|
| C4E0: | 7F | A0 | 0B | 7F | A0 | 19 | B7 | 80 | 80 | 87 | 84 | C0 | 81 | C0 | 26 | F7 | B6 | 80 | 81 | BB | A0 | 50 |
| C4F8: | B7 | A0 | 50 | 24 | 03 | 7C | A0 | 4F | 7C | 51 | B6 | 82 | BB | A0 | 0B | B7 | A0 | 0B | 24 | 03 | 7C | A0 |
| C510: | 0A | 7C | A0 | 19 | 5A | 26 | CF | BD | C6 | FE | A0 | BD | C5 | E1 | B6 | A0 | A7 | 00 | E8 | B6 | A0 | 0A |
| C528: | B7 | A0 | 4F | B6 | A0 | 0B | B7 | A0 | 50 | A0 | 19 | BD | A0 | 51 | BD | 0C | C3 | 86 | 02 | B6 | A0 | 53 |
| C540: | A7 | 00 | 39 | 86 | 20 | B7 | A0 | 1C | B6 | A0 | CA | 49 | B7 | 9A | 8D | A6 | 00 | 86 | 80 | 80 | B1 | 1C |
| C558: | 27 | 23 | B7 | 86 | 4A | B7 | A0 | EC | 4D | B6 | E3 | CA | 4D | E2 | 08 | 4A | 1F | 0C | B7 | 4A | 20 | A0 |
| C570: | 1C | B7 | 80 | 8D | 22 | 20 | 39 | 8D | BD | 8D | C6 | 00 | 74 | B7 | 39 | 86 | 8D | 32 | A6 | 26 | B6 | 39 |
| C588: | A6 | 00 | 8D | 1B | FE | 41 | 8A | 0A | 37 | 8D | 7F | A0 | 39 | A0 | FF | 20 | F7 | FE | 41 | 00 | 47 | 24 |
| C5A0: | FB | A6 | 01 | 8A | FE | 20 | 1C | 8D | B6 | 43 | 84 | E9 | 57 | CE | 20 | 01 | A7 | 20 | A6 | 39 | 43 | B6 |
| C5B8: | A0 | 43 | 8A | 20 | 20 | 05 | 8A | A0 | 20 | 8A | 84 | 24 | 15 | 8A | 06 | B6 | 43 | 0E | B6 | 33 | A0 | 84 |
| C5D0: | F9 | 8A | 04 | 43 | FD | 86 | 8A | 80 | 43 | 84 | 39 | A0 | A0 | 06 | 20 | 39 | 20 | 43 | A0 | A0 | 20 | F2 |
| C5E8: | B6 | A0 | 43 | EB | 39 | 8A | 7F | 84 | A0 | B6 | 43 | 69 | C1 | 20 | B7 | 86 | 43 | 20 | 86 | 7F | EF | 00 |
| C600: | 09 | 26 | FD | 86 | 7F | B7 | 80 | 04 | 79 | 80 | 20 | 43 | 39 | 10 | 86 | 39 | B0 | 59 | CE | 20 | 20 | 86 |
| C618: | 39 | 20 | 86 | 39 | EB | E7 | 86 | 7F | C6 | 51 | B7 | 20 | 53 | A0 | 2E | 37 | 86 | 78 | 20 | 86 | EF | 24 |
| C630: | F6 | 20 | B6 | 51 | 4F | B7 | B6 | 08 | 86 | 7F | B6 | 52 | 80 | 0F | B0 | A0 | A0 | B6 | A0 | 51 | B7 | A0 |
| C648: | 4F | 76 | A0 | 0C | 20 | A0 | 79 | 4F | B1 | 7F | 0D | 52 | A0 | 14 | 27 | 4F | B6 | 51 | B7 | 4F | 00 |
| C660: | DB | 20 | 07 | CE | A0 | A0 | A0 | 53 | 79 | 79 | 52 | 0F | 00 | 0A | 0D | 00 | A0 | 20 | A0 | A0 | 00 | 25 |
| C678: | 04 | FF | D4 | CE | FF | FF | FF | FF | FF | FF | FF | FF | FF | FF | FF | FF | FF | FF | FF | FF | 00 | 00 |

What is claimed is:

1. An imaging apparatus utilizing A.C. electrical signals generated by a thermal wave scan apparatus and indicative of the configuration of the surface and subsurface of a solid object to produce an on-line, real-time image useful in detecting the presence of surface and subsurface irregularities therein, in which a first heating energy beam is directed through the object to generate a temperature gradient, said imaging apparatus comprising:
   means for converting the A.C. electrical signals generated by the thermal wave scan apparatus to digital signals;
   memory means for storing the digital signals;
   central processing means for controlling the transfer of the digital signals to the memory means;
   means for displaying an on-line, real-time image of the surface and subsurface of the object; and
   means for generating control signals for controlling X and Y axis point deflection of the displaying means for addressing the memory means to output therefrom signals to control the intensity of each displayed point on the displaying means.

2. The imaging apparatus of claim 1, wherein the means for generating the control signals controlling the X and Y axis deflection comprises:
   counter means for generating sequential, incremental signals for addressing the memory means;
   the generated signals being used to control the X and Y axis deflection of the displaying means; and
   the generated signals also being used to address the memory means and to output therefrom the stored digital signals for controlling the intensity of each displayed point on the displaying means.

3. The imaging apparatus of claim 1, wherein the first heated energy beam is generated by a laser emitting a laser ouptut optical beam, the laser output beam having an amplitude, and modulation means for modulating the laser output beam to a pulsed beam which strikes and heats a localized point on the object, and;
   the imaging apparatus includes means for controlling the amplitude of the output beam from the modulation means.

4. The imaging apparatus of claim 1 wherein the A.C. electrical signals are generated by a thermal wave scan apparatus of a type selected from a group consisting of gas cell, photo-thermal displacement, mirage effect, infrared detection, piezoelectric detection and photoacoustic detection.

* * * * *